(12) United States Patent
Pryor et al.

(10) Patent No.: US 9,649,506 B2
(45) Date of Patent: *May 16, 2017

(54) APPARATUS AND METHODS FOR PHOTOTHERAPY

(71) Applicant: BWT Property, Inc., Newark, DE (US)

(72) Inventors: Brian Pryor, Ewing, NJ (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,532

(22) Filed: Jun. 6, 2016

(65) Prior Publication Data

US 2016/0279440 A1    Sep. 29, 2016

Related U.S. Application Data

(63) Continuation of application No. 14/537,634, filed on Nov. 10, 2014, now Pat. No. 9,358,403, which is a
(Continued)

(51) Int. Cl.
| | |
|---|---|
| *A61H 15/02* | (2006.01) |
| *A61B 18/20* | (2006.01) |
| *A61N 5/06* | (2006.01) |
| *A61N 5/067* | (2006.01) |
| *A61H 15/00* | (2006.01) |
| *A61H 99/00* | (2006.01) |
| *A61H 7/00* | (2006.01) |

(Continued)

(52) U.S. Cl.
CPC ......... *A61N 5/0616* (2013.01); *A61H 7/007* (2013.01); *A61H 15/0092* (2013.01); *A61H 15/02* (2013.01); *A61H 23/02* (2013.01); *A61H 99/00* (2013.01); *A61N 5/06* (2013.01); *A61N 5/0619* (2013.01); *A61B 18/203* (2013.01); *A61B 2018/0047* (2013.01); *A61B 2018/00452* (2013.01); *A61H 2015/0042* (2013.01); *A61H 2015/0064* (2013.01); *A61H 2201/10* (2013.01); *A61H 2201/5071* (2013.01); *A61N 2005/005* (2013.01); *A61N 2005/063* (2013.01); *A61N 2005/067* (2013.01); *A61N 2005/0644* (2013.01); *A61N 2005/0651* (2013.01)

(58) Field of Classification Search
CPC ............... A61H 15/00; A61H 15/0078; A61H 15/0085; A61H 15/0092; A61H 15/02; A61H 2015/0007; A61H 2015/0042; A61H 2015/005; A61H 2015/0064; A61H 2015/0071

See application file for complete search history.

(56) References Cited

U.S. PATENT DOCUMENTS

| | | |
|---|---|---|
| 1,844,247 A | 2/1932 | Freemon |
| 2,183,726 A | 12/1939 | Sommer et al. |
| (Continued) | | |

*Primary Examiner* — Valerie L Woodward
(74) *Attorney, Agent, or Firm* — Fish & Richardson P.C.

(57) ABSTRACT

There is provided a phototherapy apparatus, in which the therapeutic light is delivered through one or more massage components. The massage component provides mechanical massage to the subject biological tissue and modifies the properties of the subject tissue in thickness, density, etc. to facilitate the absorption of the therapeutic light and enhance the effect of the phototherapy procedure. The light source of the phototherapy apparatus is actively cooled by a synthetic jet cooler.

19 Claims, 1 Drawing Sheet

Related U.S. Application Data continuation of application No. 12/127,085, filed on May 27, 2008, now Pat. No. 8,882,685.

(51) Int. Cl.
*A61H 23/02* (2006.01)
*A61B 18/00* (2006.01)
*A61N 5/00* (2006.01)

(56) References Cited

U.S. PATENT DOCUMENTS

| | | | |
|---|---|---|---|
| 2,490,074 A | 12/1949 | Marty | |
| 2,699,771 A | 1/1955 | Ruttger-Pelli | |
| 5,336,159 A | 8/1994 | Cheng | |
| 6,056,204 A | 5/2000 | Glezer et al. | |
| 6,063,108 A | 5/2000 | Salansky et al. | |
| 6,066,129 A | 5/2000 | Larson | |
| 6,214,035 B1 | 4/2001 | Streeter | |
| 6,413,268 B1 | 7/2002 | Hartman | |
| 6,866,678 B2 | 3/2005 | Shenderova et al. | |
| 7,033,382 B2 | 4/2006 | Lach | |
| 7,052,167 B2 | 5/2006 | Vanderschuit | |
| 7,083,580 B2 | 8/2006 | Bernabei | |
| 7,083,581 B2 | 8/2006 | Tsai | |
| 7,144,247 B2 * | 12/2006 | Black | A61N 5/0603 433/29 |
| 7,264,598 B2 | 9/2007 | Shin | |
| 7,282,037 B2 | 10/2007 | Cho | |
| 7,335,170 B2 * | 2/2008 | Milne | A61H 7/001 601/15 |
| 7,749,178 B2 | 7/2010 | Imboden et al. | |
| 7,762,964 B2 * | 7/2010 | Slatkine | A61B 18/203 601/15 |
| 8,574,177 B2 | 11/2013 | Pryor et al. | |
| 8,882,685 B2 * | 11/2014 | Pryor | A61N 5/06 601/113 |
| 8,968,221 B2 * | 3/2015 | Pryor | 601/113 |
| 9,358,403 B2 * | 6/2016 | Pryor | |
| 2003/0163068 A1 * | 8/2003 | Kang | A61H 23/0245 601/15 |
| 2003/0232303 A1 | 12/2003 | Black | |
| 2004/0138727 A1 | 7/2004 | Taboada | |
| 2004/0193235 A1 | 9/2004 | Altshuler et al. | |
| 2004/0193236 A1 | 9/2004 | Altshuler et al. | |
| 2004/0236252 A1 | 11/2004 | Muzzi et al. | |
| 2004/0260209 A1 | 12/2004 | Ella et al. | |
| 2004/0260212 A1 * | 12/2004 | Cho | A61H 23/0218 601/15 |
| 2006/0235494 A1 | 10/2006 | Vanderschuit | |
| 2006/0253051 A1 | 11/2006 | Milne et al. | |
| 2007/0073366 A1 * | 3/2007 | Porco | A61H 15/02 607/89 |
| 2007/0096118 A1 * | 5/2007 | Mahalingam | F21V 29/02 257/81 |
| 2008/0014011 A1 * | 1/2008 | Rossen | A45D 34/041 401/195 |
| 2008/0262394 A1 | 10/2008 | Pryor et al. | |
| 2009/0001372 A1 * | 1/2009 | Arik | C09K 5/10 257/58 |
| 2009/0234253 A1 * | 9/2009 | Vandenbelt | A46B 13/023 601/15 |
| 2009/0299236 A1 | 12/2009 | Pryor et al. | |
| 2011/0144725 A1 | 6/2011 | Pryor et al. | |
| 2015/0174424 A1 * | 6/2015 | Pryor | A61H 7/007 601/18 |

* cited by examiner

APPARATUS AND METHODS FOR PHOTOTHERAPY

FIELD OF THE INVENTION

This invention relates to apparatus and methods for phototherapy.

BACKGROUND

Phototherapy relates to treatment of biological tissues, such as skin tissues, using visible, ultraviolet, and/or infrared lights. The light treatment may be applied solely for sterilization, pain relief, bio-modulation, and photo-rejuvenation. Alternatively, the treatment may be used in combination with certain photo-sensitive drugs or nutrition supplements. In comparison with laser surgery, the light intensity employed in phototherapy is much lower. Thus the light sources used in phototherapy are not limited to lasers but may include light emitting diodes (LEDs) and/or certain types of lamps as well. Typical applications of phototherapy include wound healing, cellulite reduction, skin rejuvenation, pain relief, fat reduction and contouring, laser acupuncture, pressure ulcer treatment, etc.

It is well known in the prior art that phototherapy may be applied in combination with mechanical massage. Some examples can be found in U.S. Pat. No. 7,033,382 to Lach; and U.S. Patent Application Nos. 20060253051 to Milne et al, 20060235494, 20040236252 to Muzzi et al, and 20070073366 to Porco. However, none of the prior art suggests to apply phototherapy with mechanical massage in a concerted manner, where phototherapy and mechanical massage are applied to the same target area and benefit from each other thereby producing significantly improved therapeutic results. Furthermore, none of the prior art discloses a compact phototherapy/massage wand design, which provides effective heat dissipation for the high power lasers/LEDs yet maintains a small size and weight that can be easily handled by the practitioner.

SUMMARY OF THE INVENTION

According to one aspect of the present invention, there is provided a phototherapy apparatus, wherein the therapeutic light is delivered through one or more massage components. The massage component provides mechanical massage to a subject biological tissue and modifies the properties of the subject tissue in thickness, density, local pressure, micro-circulation, etc. to facilitate the absorption and interaction of the therapeutic light with the subject tissue and enhance the effect of the phototherapy procedure. Meanwhile, the therapeutic light in its interaction with the illuminated tissue also facilitates and enhances the effect of the mechanical massage.

According to another aspect of the present invention, a piezoelectric based synthetic jet actuator is utilized to provide efficient thermal management for the light source of the phototherapy apparatus. The synthetic jet actuator features extremely low noise, low power consumption, and greatly extended lifetime.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1A:
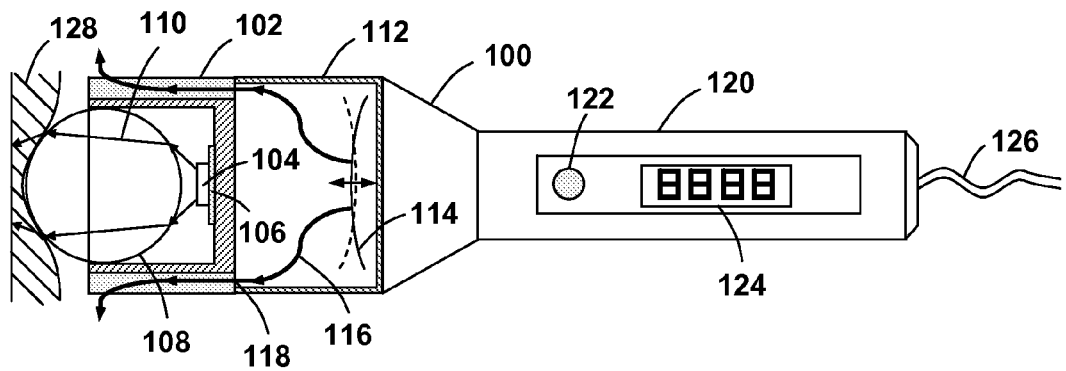
FIG. 1a illustrates a cross section view of one exemplified embodiment of the phototherapy apparatus, in which the therapeutic light is delivered through a transparent massage ball.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to phototherapy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1B:
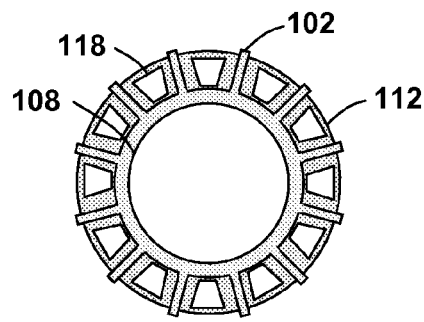
FIG. 1b illustrates a top view of the phototherapy apparatus of FIG. 1a from the side of the massage ball.

In the first embodiment of the present invention as shown in FIG. 1a and FIG. 1b, the phototherapy apparatus 100 is in the form of a phototherapy/massage wand comprising an optical head 102, a synthetic jet cooler 112, and a handle 120. The optical head 102 holds a laser or light emitting diode (LED) light source 104 and a rolling massage ball 108. The massage ball 108 may rotate freely in all directions (a 360° freedom of movement) in the optical head 102 with controlled friction. The massage ball 108 is transparent at the wavelength of the therapeutic light 110 that is produced by the light source 104. Thus the therapeutic light 110 can transmit through the massage ball 108 to the subject biological tissue 128 to be treated. It is also possible to incorporate a group of optical elements between the light source 104 and the massage ball 108 for controlling the divergence angle, intensity distribution, uniformity, beam size, etc. of the therapeutic light 110. The light source 104 is preferably a high power semiconductor laser or LED, such as a class IV semiconductor laser mounted on a thermal conductive substrate 106. The substrate 106 is further mounted on the optical head 102, which is also made of thermal conductive material and comprises an array of fins along its outer circumference for dissipating the heat produced by the light source 104.

The optical head 102 is mechanically coupled with a synthetic jet cooler 112, which comprises a piezoelectric actuator 114 and an array of ventilation holes 118 matching with the array of fins of the optical head 102. The periodic vibration of the piezoelectric actuator 114 produces a periodic jet of air flow 116 through those ventilation holes 118, which carries away the heated air around the circumference of the optical head 102. Comparing with conventional fans, this synthetic jet cooler is more efficient since the jet of air flow can be accurately directed toward the hot spot. In addition, the synthetic jet cooler offers much lower noise level, lower power consumption, and greatly extended lifetime.

The handle 120 of the phototherapy apparatus 100 comprises a group of control buttons 122 and a display unit 124 used to control and displays the on/off status and power level of the light source 104. The control buttons 122 and the display unit 124 are electrically connected to a drive/control circuit board (not shown) contained in the handle 120, which provides electric power and control signal to the light source 104 and the piezoelectric actuator 114. The drive/control circuit board is further powered through a wire 126 connected to a wall plug (not shown). In a slight variation of the present embodiment, the drive/control circuit board may be powered by batteries or rechargeable batteries.

Through the handle 120, a practitioner can applied a force to the massage ball 108, causing it to roll on the subject biological tissue 128 (such as skin tissue) and deliver a pressure on the tissue in contact with the massage ball 108. On one hand, this rolling and kneading action causes an increase in blood circulation and fluid mobilization of the subcutaneous tissue, smoothes and firms the subject anatomy. Thus lipolysis is restored and fat cell metabolism is reactivated, resulting in the reduction of fat tissue and smoothing of cellulite. It also can help for the relief of muscle aches and pain. On the other hand, the action also causes a reduction in tissue thickness and an increase in tissue density. This change in tissue property helps to reduce the overall absorption and scattering loss of the therapeutic light 110 and allows the therapeutic light 110 to penetrate deeper into the tissue and induce stronger photochemical processes, e.g. increase of ATP (adenosine triphosphate), triggering of photo neurological response and activation of enzymes, changes in local pressure, increases in temperature and permeability of cellular membranes. Since the massage ball 108 is in contact with the subject tissue 128, the therapeutic light 110 will penetrate into the subject tissue 128 directly with no air interface. This feature allows the practitioner to control the intensity of the delivered therapeutic light in a more accurate manner. The photo biomodulation in turn helps to enhance the effect of the mechanical massage by stimulating inter or intra cellular response, increasing micro-circulation, etc.

In another variation of the present embodiment, the massage ball may have a diffusive or scattering optical surface, which is capable of spreading the transmitted light into various angles and directions. The diffusive surface can be prepared by forming some type of micro-structures or by coating a layer of diffusive optical material on the surface of the massage ball. When the massage ball is not in contact with the subject tissue, the therapeutic light is diffused by the diffusive surface as it transmits from the massage ball into air. Thus the transmitted light has an increased spread angle and hence a reduced light intensity when viewed from a distance away. This reduction in viewed light intensity enhances the safety level of the phototherapy apparatus. In comparison, when the massage ball is in contact with the subject tissue, the transmitted light is much less distorted or spread. This is due to the fact that the tissue in contact with the surface of the massage ball serves as an optical index matching medium which effectively reduces diffusing or scattering cause by the massage ball surface. Hence, the light beam is effectively delivered into the tissue with desired direction, angle, power density, depth, and intensity distribution. As another variation, certain optical index matching liquids, gels, suspension particles, powders may be applied between the massage ball and the subject tissue to further enhance light transmittance and reduce the light distortion caused by the massage ball surface. Those optical index matching media may also have therapeutic or pharmaceutical effect to further improve the effect of phototherapy.

In yet another variation of the present embodiment, the massage ball (or simply an optical window with curved surface) is rigidly affixed to the optical head and moves together or in unison with the optical head. In this variation, the mechanical massage is performed by kneading the subject tissue with the massage ball without the rolling action.

In yet another variation of the present embodiment, a motor is installed in the optical head and mechanically coupled to the massage ball to generate rolling, kneading, and/or vibration movements of the massage ball.

One application of the phototherapy apparatus 100 is relieving the pain associated with migraine headaches, in which therapeutic light is delivered through the transparent massage ball to the forehead, temples, paranasal sinus, and/or neck of the patient. The optical properties of the massage ball, such as its refractive index, diameter or curvature, etc. can be utilized to shape the light beam to an ideal spot size or value. The phototherapy apparatus 100 may further comprise a touch sensor or a pressure sensor (both not shown), such as a spring loaded device feature to control the on/off status of the light source in such a way that the light source can only be turned on when the massage ball touches the skin tissue. This helps to improve the safety of laser treatments around the eye by limiting the chance of laser exposure to the eye directly. Other applications of the phototherapy apparatus 100 comprise cellulite reduction, skin rejuvenation, pain relief, fat reduction and/or contouring, laser acupuncture, wound healing, and/or pressure ulcer treatment.

In the foregoing specification, specific embodiments of the present invention have been described. However, one of ordinary skill in the art appreciates that various modifications and changes can be made without departing from the scope of the present invention as set forth in the claims below. For example, the therapeutic light source and the massage component are not limited to the presently disclosed forms. The massage component can take any other geometrical forms in addition to the spherical shape as disclosed. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A phototherapy apparatus comprising:
a rolling massage component comprising a curved surface configured for contact with skin tissue;
a light source spaced apart from the rolling massage component, wherein light emitted from the light source is delivered onto an outer surface of the rolling massage component and is transmitted through the rolling massage component; and
a cooling device.

2. The phototherapy apparatus of claim 1, wherein the rolling massage component comprises a ball that is rotatable in all directions.

3. The phototherapy apparatus of claim 1, wherein the rolling massage component comprises a diffusive optical surface for increasing a spread angle of the light.

4. The phototherapy apparatus of claim 1, wherein the light source comprises a high power laser or a high power light emitting diode (LED).

5. The phototherapy apparatus of claim 1, wherein the cooling device comprises a synthetic jet cooler.

6. The phototherapy apparatus of claim 1, further comprising a motor configured to generate a movement of the rolling massage component.

7. The phototherapy apparatus of claim 1, further comprising a handle including a display unit and control buttons, wherein the rolling massage component, the light source, and the cooling device are each coupled to the handle.

8. The phototherapy apparatus of claim 1, further comprising a means for preventing activation of the light source unless the rolling massage component is in contact with the skin tissue.

9. The phototherapy apparatus of claim 1, wherein the light emitted from the light source comprises infrared light and the rolling massage component is adapted to transmit the infrared light.

10. A method for phototherapy treatment, the method comprising:
applying a phototherapy apparatus to a skin surface, wherein the phototherapy apparatus comprises:
a rolling massage component comprising a curved surface configured for contact with skin tissue;
a light source spaced apart from the rolling massage component; and
a cooling device,
wherein light emitted from the light source is delivered onto an outer surface of the rolling massage component and is transmitted through the rolling massage component to the skin surface,
wherein at least a portion of the curved surface contacts the skin surface to provide a massaging action that compresses tissue below the skin surface to allow the light emitted from the light source to penetrate deeper into the tissue.

11. The method of claim 10, wherein the rolling massage component comprises a ball.

12. The method of claim 10, wherein the rolling massage component comprises a diffusive optical surface for increasing a spread angle of the light.

13. The method of claim 10, wherein the light source comprises a high power laser or a high power light emitting diode (LED).

14. The method of claim 10, wherein the cooling device comprises a synthetic jet cooler.

15. The method of claim 10, wherein the phototherapy apparatus further comprises a motor configured to generate a movement of the rolling massage component.

16. The method of claim 10, wherein the phototherapy apparatus further comprises a handle including a display unit and control buttons, wherein the rolling massage component, light source, and cooling device are each coupled to the handle.

17. The method of claim 10, wherein the phototherapy apparatus further comprises a means for preventing activation of the light source unless the rolling massage component is in contact with the skin tissue.

18. The method of claim 10, wherein at least some of the massaging action occurs while the light is transmitted to the skin surface.

19. The method of claim 10, wherein the light emitted from the light source comprises infrared light and the rolling massage component is adapted to transmit the infrared light.

* * * * *